(12) United States Patent
Dusek et al.

(10) Patent No.: US 10,085,882 B2
(45) Date of Patent: Oct. 2, 2018

(54) OCULAR LENS CAPSULE RETAINER

(75) Inventors: Vaclav Dusek, Bellevue, WA (US);
Lawrence Laks, Bellevue, WA (US);
Robert May, Redmond, WA (US);
Natalya Peskin, Redmond, WA (US);
Steven Wesley Smith, Redmond, WA (US)

(73) Assignee: Microsurgical Technology, Inc., Redmond, WA (US)

( * ) Notice: Subject to any disclaimer, the term of this patent is extended or adjusted under 35 U.S.C. 154(b) by 1250 days.

(21) Appl. No.: 13/635,888

(22) PCT Filed: Mar. 22, 2011

(86) PCT No.: PCT/US2011/029451
§ 371 (c)(1),
(2), (4) Date: Oct. 9, 2012

(87) PCT Pub. No.: WO2011/119621
PCT Pub. Date: Sep. 29, 2011

(65) Prior Publication Data
US 2013/0197533 A1   Aug. 1, 2013

Related U.S. Application Data

(60) Provisional application No. 61/405,552, filed on Oct. 21, 2010, provisional application No. 61/316,339, filed on Mar. 22, 2010.

(51) Int. Cl.
*A61F 9/00* (2006.01)
*A61F 9/007* (2006.01)
(Continued)

(52) U.S. Cl.
CPC ............ *A61F 9/0008* (2013.01); *A61B 50/20* (2016.02); *A61B 50/30* (2016.02);
(Continued)

(58) Field of Classification Search
CPC .... A61F 9/0008; A61F 9/00736; A61F 9/007; A61F 9/00754; A61F 9/00763; A61B 19/0256; A61B 19/026; A61B 2019/0202; A61B 2017/00526; A61B 17/22; A61B 17/32037; A61B 17/32056
See application file for complete search history.

(56) References Cited

U.S. PATENT DOCUMENTS

| | | | | |
|---|---|---|---|---|
| 4,190,042 A | * | 2/1980 | Sinnreich | A61B 1/32 600/204 |
| 5,171,233 A | * | 12/1992 | Amplatz | A61B 17/221 604/540 |

(Continued)

OTHER PUBLICATIONS

International Search Report and Written Opinion dated Dec. 23, 2011, issued in corresponding International No. Application PCT/US2011/029451, filed Mar. 22, 2011, 6 pages.

*Primary Examiner* — Thomas McEvoy
(74) *Attorney, Agent, or Firm* — Knobbe Martens Olson & Bear LLP

(57) ABSTRACT

A thin resilient strand, such as medical suture material, extends from a stiffer shank. The strand can form a resilient hook and/or it can have an arcuate free end to engage tissue such as the interior of a capsular bag at approximately its equator during ophthalmic surgery.

19 Claims, 16 Drawing Sheets

(51) Int. Cl.
*A61B 50/20* (2016.01)
*A61B 50/30* (2016.01)
A61B 17/00 (2006.01)
A61B 50/00 (2016.01)

(52) U.S. Cl.
CPC ............... *A61F 9/00736* (2013.01); *A61B 2017/00526* (2013.01); *A61B 2050/005* (2016.02)

(56) References Cited

U.S. PATENT DOCUMENTS

| | | | | |
|---|---|---|---|---|
| 5,290,292 | A * | 3/1994 | Householder | A61B 17/0231 600/209 |
| 5,807,244 | A * | 9/1998 | Barot | A61B 17/0231 600/236 |
| 6,428,501 | B1 | 8/2002 | Reynard | |
| 6,561,974 | B1 * | 5/2003 | Grieshaber | A61B 17/0231 600/206 |
| 8,425,595 | B2 * | 4/2013 | Tsai | A61F 2/1648 623/6.12 |
| 2003/0014106 | A1 | 1/2003 | Kita | |
| 2003/0196922 | A1 * | 10/2003 | Reaux | A61B 17/06161 206/370 |
| 2004/0230203 | A1 * | 11/2004 | Yaguchi | A61F 2/16 606/107 |
| 2006/0018949 | A1 | 1/2006 | Ammon, Jr. | |
| 2009/0054904 | A1 * | 2/2009 | Holmen | A61B 17/320016 606/107 |
| 2009/0192478 | A1 | 7/2009 | Soroudi | |

* cited by examiner

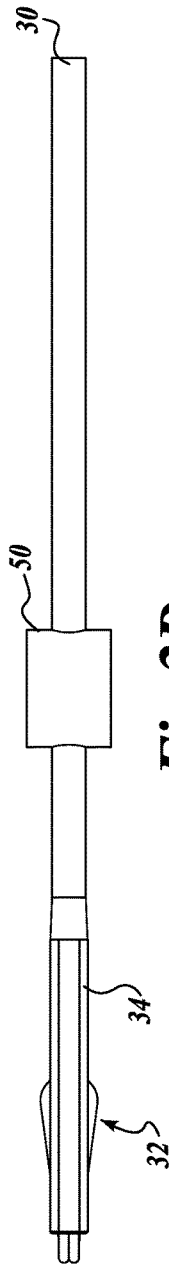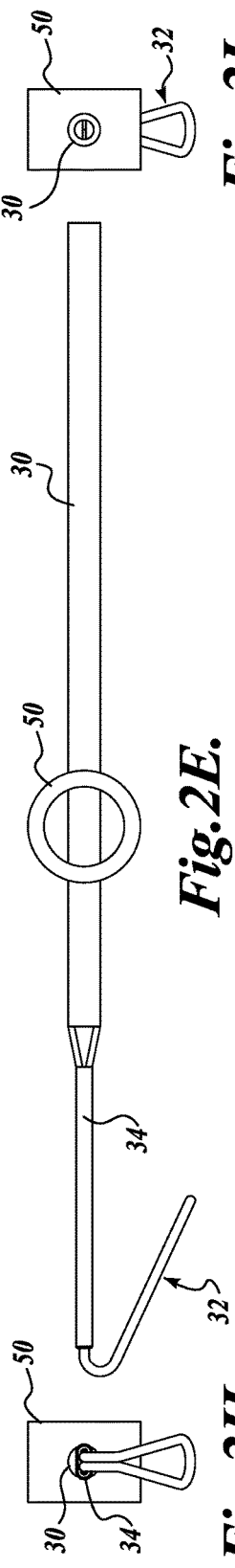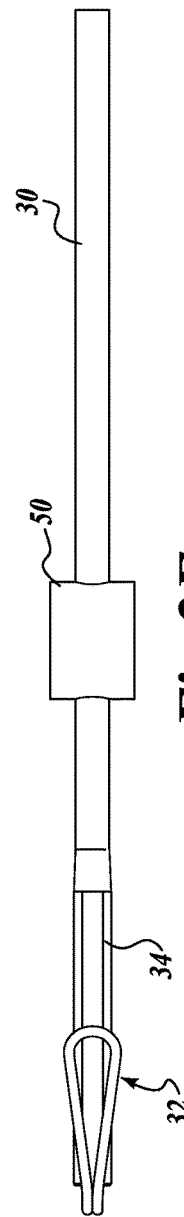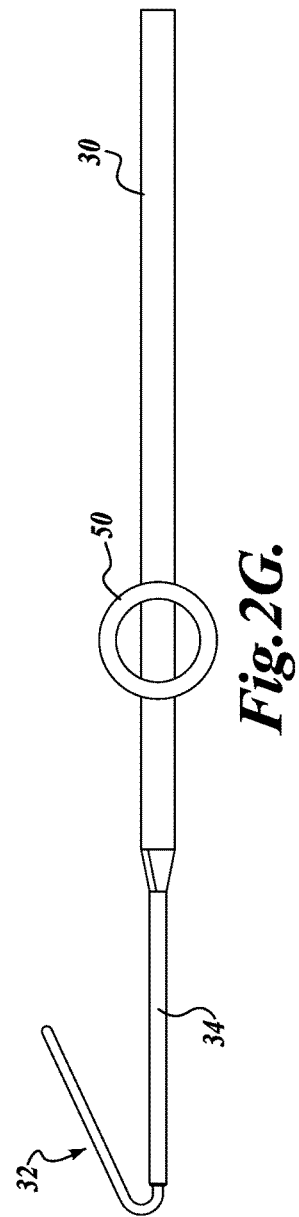
Fig. 2D. Fig. 2E. Fig. 2F. Fig. 2G. Fig. 2H. Fig. 2I.

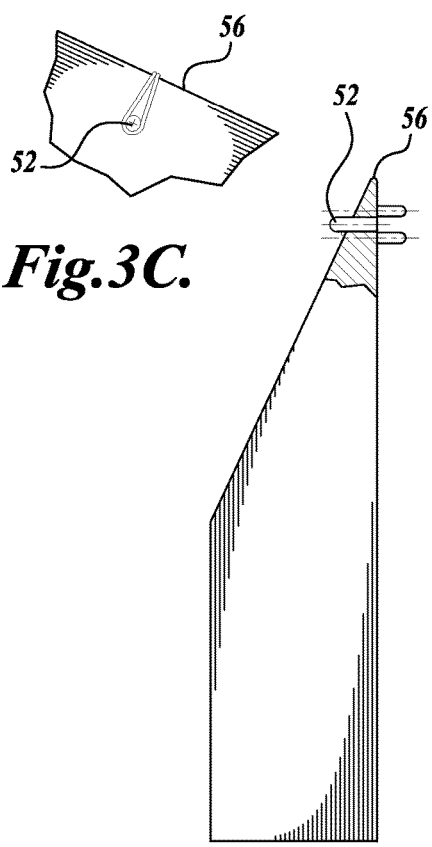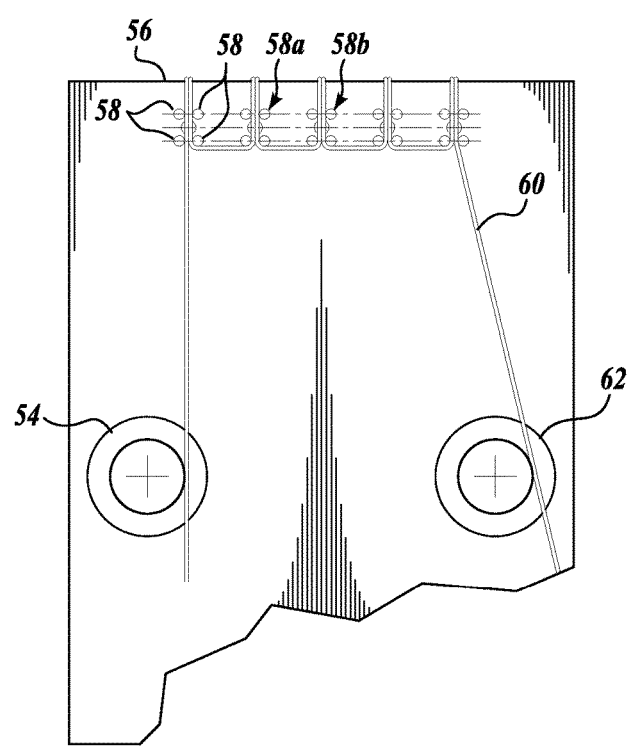
Fig.3C.
Fig.3A.
Fig.3B.

OCULAR LENS CAPSULE RETAINER

CROSS-REFERENCES TO RELATED APPLICATIONS

This application claims the benefit of U.S. Provisional Application No. 61/316,339, filed Mar. 22, 2010, and U.S. Provisional Application No. 61/405,522, filed Oct. 21, 2010, the disclosures of which are incorporated by reference herein.

BACKGROUND

The present invention pertains generally to instruments used in intraocular ophthalmic surgery within the lens capsule (referred to herein as intracapsular ophthalmic surgery, not to be confused with the specific procedure sometimes called intracapsular cataract extraction of ICCE), and in one aspect of the invention to instruments for retaining the lens capsule in a stable, centered position during surgery.

In modern cataract surgery, a short incision is made along the margin of the cornea for access to the lens through the central opening of the iris (pupil). A circular opening is cut or torn in the anterior capsule (capsularhexis), and in the case of a cataract, the clouded lens is removed, such as by phacoemulsification. Preferably, the posterior portion of the lens capsule is left intact so that the posterior chamber remains isolated from the vitreous. Also, the zonules are not disturbed so that the opened lens capsule continues to be supported and centered in the posterior chamber. Thereafter, an artificial lens is implanted in a manner well known in the art.

Aging results in changes in characteristics of various parts of the eye, such as the zonules. The centering force of the zonules is not strong. Over time, the zonules can become weaker or may be partly missing, thus less reliable in centering the capsule beneath the iris because different forces may be applied at opposite sides of the capsule. This can create a problem for the surgeon because performing the lens replacement may be more difficult if the lens capsule is not centered, and the surgery itself may introduce unnatural stresses that could damage weak or brittle zonules.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one embodiment an instrument in accordance with the present invention has a rigid or stiffened shank intermediate portion, usable as a handle. A distal part extends from the shank intermediate portion and can be straight or form a reflex bend. A resilient strand extends from the distal part. The strand can form a resilient hook and/or it can have an arcuate free end to engage tissue such as the interior of a capsular bag at approximately its equator. The arcuate end can be formed by a loop of the strand material. The strand can extend from a hollow rigid cannula or the strand can have side-by-side stretches that are encased in stiffening material, such as heat-shrinkable plastic, to form the core of the shank intermediate portion. The strand can be heat formed to a desired shape while tensioned on a jig, and can be packaged in a cavity of a preformed base with an end grasped by a mounting bar from which it is cantilevered to extend in the cavity, out of contact with the surrounding walls.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 2D-2I are orthographic projections of the instrument of FIG. 1, namely: FIG. 2D is a top plan thereof; FIG. 2E is a left side elevation thereof; FIG. 2F is bottom plan thereof; FIG. 2G is a left side elevation thereof; FIG. 2H is a distal end elevation thereof; and FIG. 2I is a proximate end elevation thereof;

FIG. 3A is a side elevation of a tool used in the manufacture of the instrument of FIG. 1, with parts broken away; FIG. 3B is a diagrammatic top plan view thereof, with parts broken away; and FIG. 3C is a fragmentary, oblique, bottom projection thereof;

DETAILED DESCRIPTION

Figure 1:
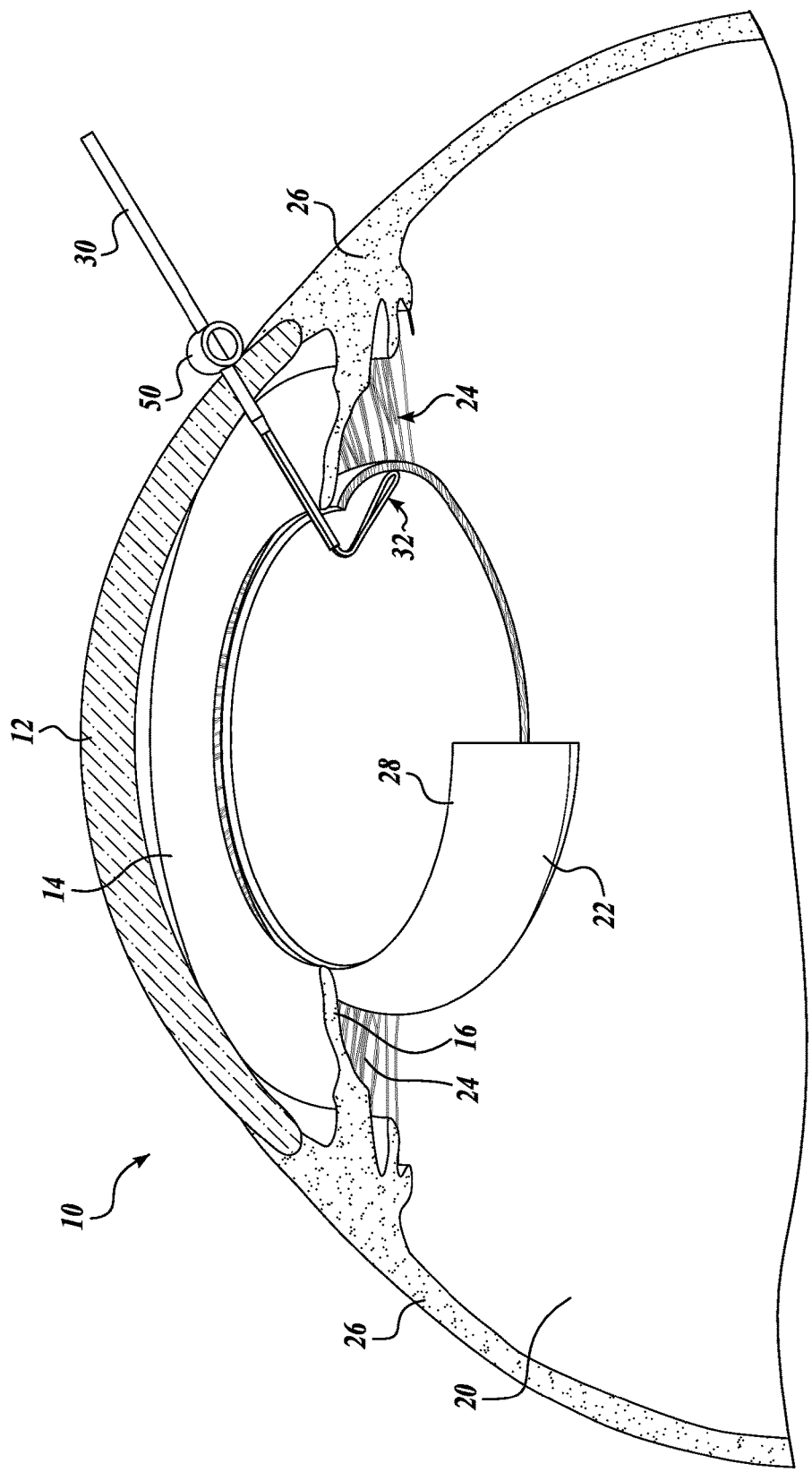
FIG. 1 is an enlarged, fragmentary, diagrammatic illustration of a human eye ball with parts broken away for ease of illustration and explanation, and with an instrument in accordance with the present invention positioned for use during ophthalmic surgery.

FIG. 1 is a greatly enlarged, fragmentary, diagrammatic illustration of a human eyeball with parts broken away for ease of illustration and explanation. Moving from the exterior toward the center, the eye 10 includes the cornea 12, anterior chamber 14 behind the cornea, the iris 16, posterior chamber behind the iris, and vitreous body 20 which encompasses the major portion of the volume of the eyeball. The lens (not shown in FIG. 1) is located in the posterior chamber, between the iris and the vitreous body, and consists of a relatively hard central nucleus surrounded by the softer cortex, all enclosed in a membrane called the capsule 22, or more informally, the "bag." The capsule and lens structure are held in position behind the iris by fibers called zonules 24 that extend between the lens capsule and the periphery of the posterior chamber, i.e., to the sclera 26 which is the "white of the eye" that forms part of the supporting wall of the eyeball below the cornea.

In general, as represented in FIG. 1, a first embodiment of an instrument in accordance with the present invention has a small diameter shaft 30 which preferably is strong, straight, and tubular, and a separate resilient strand 32 which is formed in a loop for engaging against the inside periphery of the capsule at approximately its equator. One, two or more of the instruments can be used to retain a lens capsule in a desired position during surgery for both centering the capsule and providing additional support for the zonules. The instrument is extremely small.

Figure 2A:
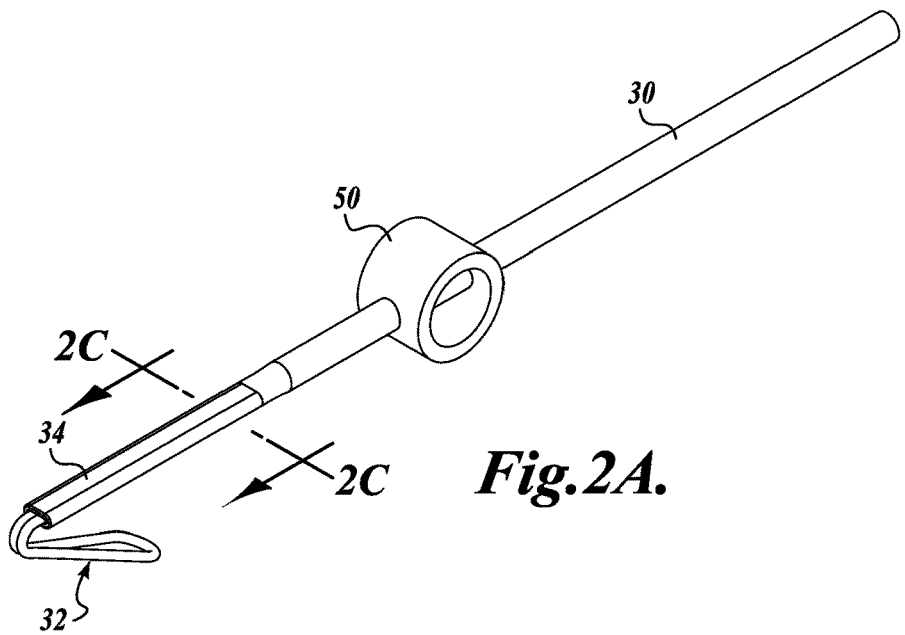
FIG. 2A is a further enlarged top perspective of the instrument of FIG. 1 looking generally in a distal direction.

The first embodiment of the present invention is shown in more detail in FIGS. 2A-2I. Referring to FIG. 2A, the shaft 30 (also referred to as the elongated intermediate shank) of the instrument can be a rigid tube or cannula, such as 25 gauge or 26 gauge stainless steel cannula. In this embodiment the proximate end portion is colinear with the intermediate shank portion. In the case of a 25 gauge stainless steel cannula the outside diameter is 0.5 mm, or 0.020 inch. The wall thickness is typically 0.004 inch, leaving an inside diameter of 0.012 inch. The distal end portion 34 of the cannula is flattened, such as to a thickness of 0.25 mm or 0.010 inch, forming a shorter and wider outer and inner diameter. The resilient strand 32 of the instrument projects from the distal end of the flattened section 34 and can be formed from surgical plastic suture, preferably nylon, as described in more detail below, such as 4-0 or 5-0 nylon suture. Consequently, the shaft has a stiffness much greater than the inherent resiliency of the strand.

Figure 2B:
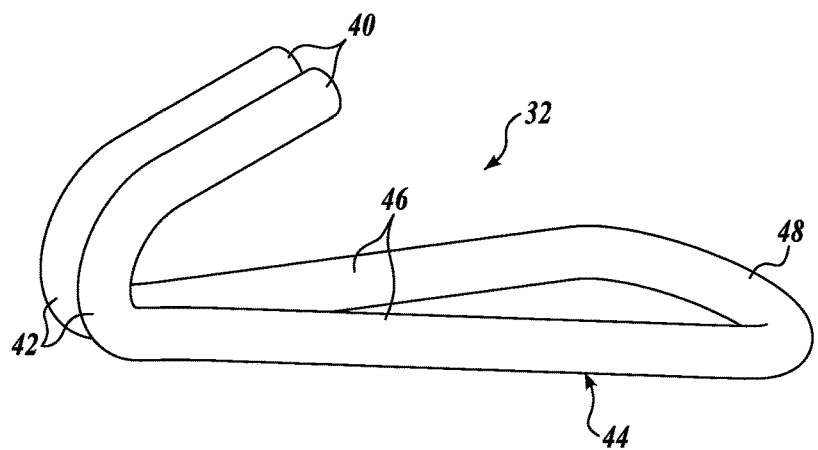
FIG. 2B is a further enlarged perspective of the distal end component of such instrument.
Figure 2C:
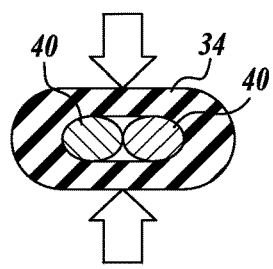
FIG. 2C is a diagrammatic section of such instrument taken along line 2C-2C of FIG. 2A.

With reference to FIG. 2B, the resilient strand 32 has short opposite ends 40 extending side-by-side to be fitted within the flattened cannula section 34. The cannula can then be crimped to secure the resilient member to the shaft 30, 34 as represented in FIG. 2C. Returning to FIG. 2B, the short straight ends 40 extend distally to corresponding reflex bends 42 such that the cantilevered resilient end portion 44 extends back proximally at an acute angle to the shaft 30, 34, preferably 20° to 40° (the portions 40 and bend 44 of the strand are sometimes referred to as the distal end portion of the instrument). From the reflex bends the side-by-side stretches 46 of the suture diverge to form a narrow loop with a blunt arcuate end portion 48 for engagement against the inside of the lens capsule at approximately its equator. The length of the loop is chosen so that in a typical surgical procedure the loop end 48 engages the inner periphery of the capsule near the equator and can deform to apply a gentle pressure to center and/or stabilize the capsule without unduly pulling against the iris or the margin of the opening cut in the anterior capsule. In a representative embodiment this length can be 2.50 mm to 3.50 mm, with 3.17 mm currently being preferred.

As noted above, the dimensions in the drawings are exaggerated for ease of illustration and description. The distal tip portion of the instrument can be inserted through a corneal slit no more than 1 mm wide. The loop 32 is sufficiently resilient that it will bend inward as it passes through the slit, but with sufficient memory that it then relaxes to the condition shown in the drawings. The shaft 30 is then pulled back to the condition shown in FIG. 1 to position the resilient member 32 to apply the desired force against the inner periphery of the capsule. When the desired position is achieved, an adjustable stopper 50 can be slid along the shaft 30 to engage the cornea adjacent to the slit through which the tool is inserted. The stopper can be a comparatively large resilient cylinder that, although adjustable, is sufficiently frictionally engaged with the shaft to retain the tool in position during the surgery.

The desired shape of the resilient member and its loop can be obtained by tensioning the suture material on a positioning tool and maintaining it in that shape while heat treating to approximately the softening temperature, which typically is about 200° C. to 250° C. for nylon suture. For example, a resilient strand in accordance with FIG. 2B can be formed on a jig of the type shown in FIGS. 3A, 3B, and 3C. The side elevational view of FIG. 3A shows the tool diagrammatically, including an upright pin 52, also seen in the oblique projection of FIG. 3C. The top side of the tool is seen in FIG. 3B, with parts again shown diagrammatically. The tool is designed for forming five resilient strand members at a time. One end of a length of the suture material is clamped to the top side of the tool by a screw 54. The suture is tensioned and fitted between two pair of rearwardly projecting pegs 58. The pegs 58 of each pair are spaced apart a distance approximately equal to twice the diameter of the suture, and the two pair of back pegs are centered over the corresponding pin 52 that projects from the other (bottom) side. From the pegs 58, the suture is wrapped around the tip 56 of a wedge section of the tool, then down and around the corresponding pin 52, as best seen in FIG. 3C. After being wrapped around a pin 52, the suture is wound back up around the tip 56 and between the same pegs 58 through which it extends in the other direction, such that in this location the suture stretches are contiguously engaged in the side-by-side relationship.

From the first set of pegs 58, the suture can be wound to and between the next set represented at 58a in FIG. 3B, then around the tip 56 of the wedge and the next pin 52, back around the tip 56 and through the pairs of pegs 58a, to the next set of pegs 58b, and so on. The final stretch 60 of the suture is tensioned and clamped by a screw 62. With the suture thus positioned, it is heat treated in an oven at approximately the softening temperature, typically 200° C. to 250° C., for 5-8 minutes. Upon cooling, the five separate loops can be cut at the rear of the tool near the pegs 58 closest to the tip 56, resulting in five of the resilient members 32 of the type shown in FIG. 2B. The size and shape of the loop is determined by the size and shape of the front pin 52. In a representative embodiment the pin can be sized so that the maximum outside diameter of the loop is less than 1 mm, for example 0.86 mm in a representative embodiment.

Figure 4:
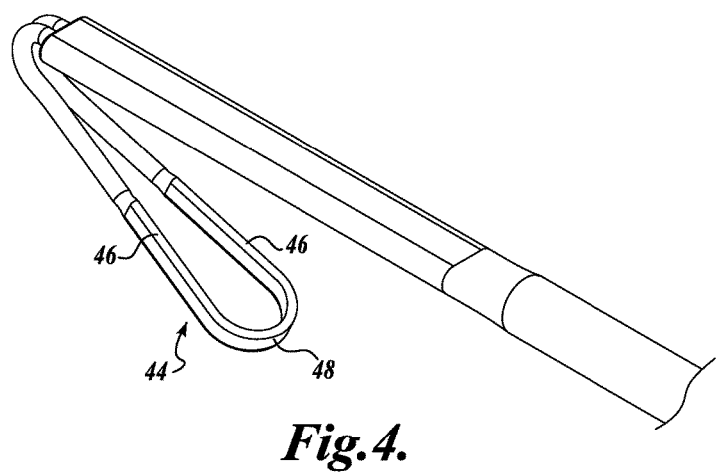
FIG. 4 is a fragmentary perspective of a modified instrument in accordance with the present invention, viewed from the top and toward the distal end portion thereof.

The embodiment of FIG. 4 is identical to the embodiment of FIGS. 2A-2I except that the sides 46 and curved end 48 of the resilient loop 44 are flattened either during or following the heat-forming process. If after, the sides and curved end of the suture can be mechanically flattened, such as with specialized pliers or a vice-like tool, or possibly by abrasion. If during the heat-forming process, the top pin can be teardrop shaped and mechanical pressure can be applied to press the suture against the pin. Changing the shape either after or during the heat-treating process may change the mechanical characteristics such as the resiliency or springiness of the loop to achieve a desired application of force against the inner periphery of the lens capsule during use of the instrument.

Figure 5:
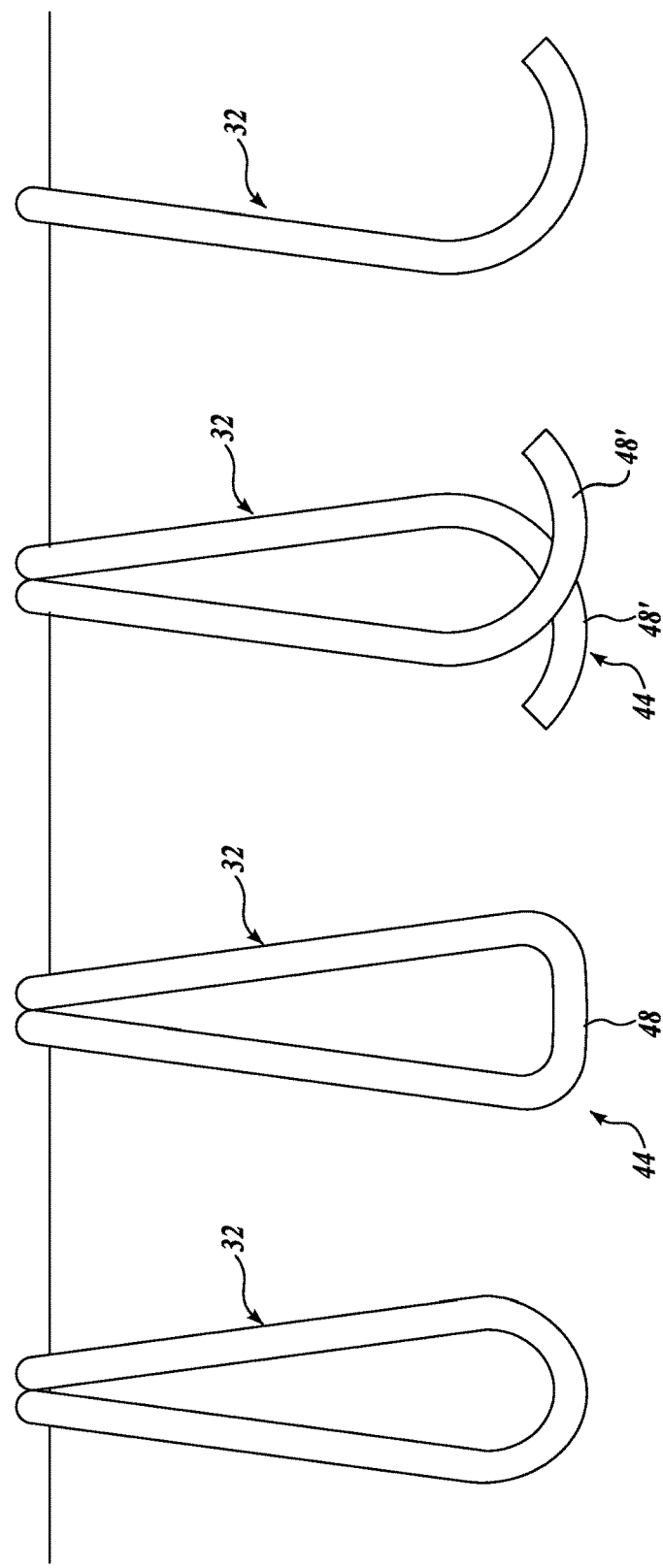
FIG. 5 is a diagrammatic bottom plan illustrating additional modifications for an instrument in accordance with the present invention, namely, alternative constructions and shapes for a resilient strand portion thereof.

FIG. 5 shows additional embodiments for the resilient strand component 32, the embodiment of FIG. 2B being shown at the left. In the embodiment shown at the center-left position, the loop portion 44 of the resilient component has a less sharply curved end 48 which can be only slightly rounded (approximately 6 mm radius) to approximate the curvature of the capsule near its equator (typically about 11 mm diameter). This is achieved by winding on a pin of the same shape and then heat treating. For the embodiment shown at the center-right position of FIG. 5, the loop portion 44 of the resilient strand component 32 is severed so that oppositely projecting arcs 48' are formed which increase the surface area of the inner periphery of the capsule engaged by the resilient strand member during use. In the embodiment at the right, a single strand is used for a more resilient, and more gentle, application of force, but with the blunt arc of strand material at the end. In the orientation of FIG. 5, the top ends of the suture are at the location of the reflex bends and lead back to the short stub portion or portions fitted into the end of the rigid cannula.

Figure 6:
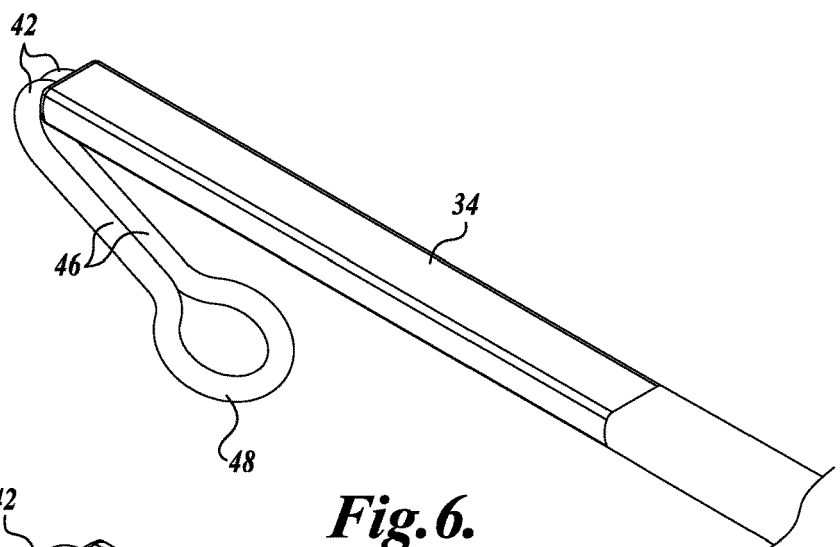
FIG. 6 is a fragmentary perspective of another modified instrument in accordance with the present invention viewed from the top and toward the distal end portion.

FIG. 6 is another embodiment similar to the embodiment of FIG. 2B in that closely adjacent, side-by-side stub sections are fitted in the flattened distal end 34 of the cannula and secured. Each stub leads to a reflex bend 42 but, unlike the previously described embodiments, the stretches 46 do not diverge but rather extend closely adjacent to each other to a smaller looped eye portion. This embodiment can be formed by use of pins and pegs at the top of a jig (of the general type shown in FIGS. 3A-3C) which maintain the desired shape during heat treatment.

Figure 7:
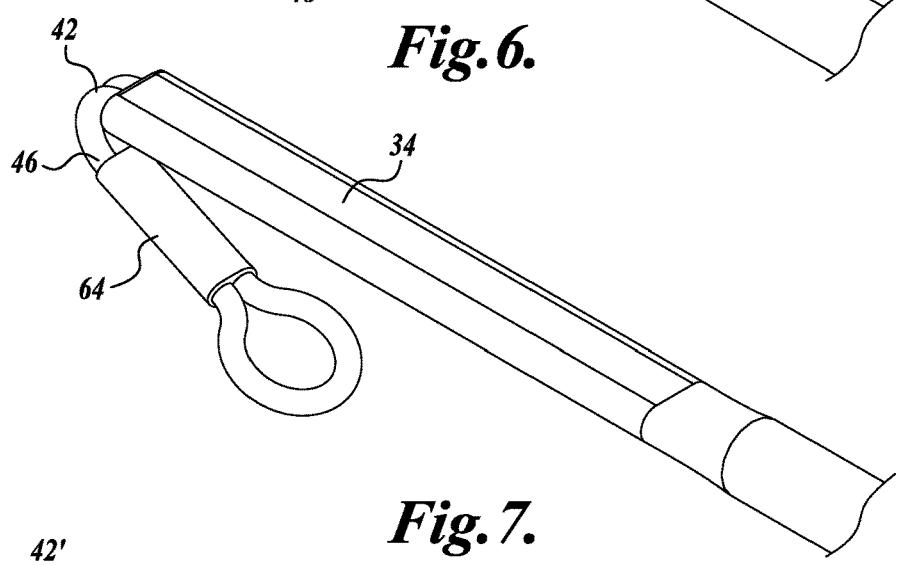
FIG. 7 is a corresponding perspective of another modified instrument in accordance with the present invention.

The embodiment of FIG. 7 is identical to the embodiment of FIG. 6 except that the straight stretches 46 of the suture are encased in medical grade heat-shrinkable tubing or film 64, preferably polyester, extremely thin, to assist in maintaining the straight stretches of suture together. The heat-shrinkable tubing or film can be applied following formation of the resilient member by the heat-forming process.

Figure 8:
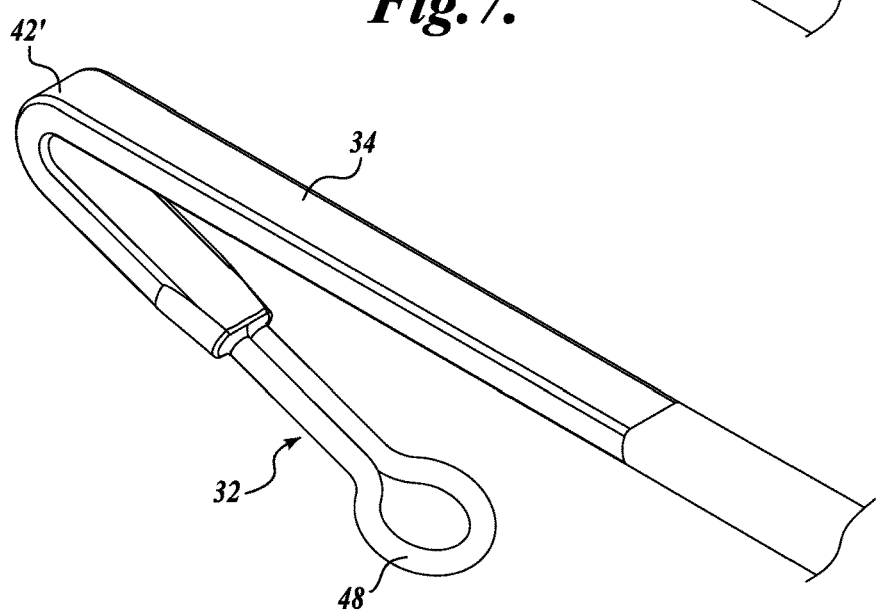
FIG. 8 is a corresponding perspective of yet another modified instrument in accordance with the present invention.

In the embodiment of FIG. 8, the flattened section 34 of the shaft is extended and has the desired reflex bend 42' so as to form the distal portion of the instrument. The resilient strand member 32 extends straight from the reflex bend to an end loop 48, and can be formed from surgical plastic suture as previously described. Alternatively, a more nearly teardrop shape may be achieved by simply inserting the opposite ends of the suture material into the flattened section prior to crimping, with no previous heat treatment.

Figure 9:
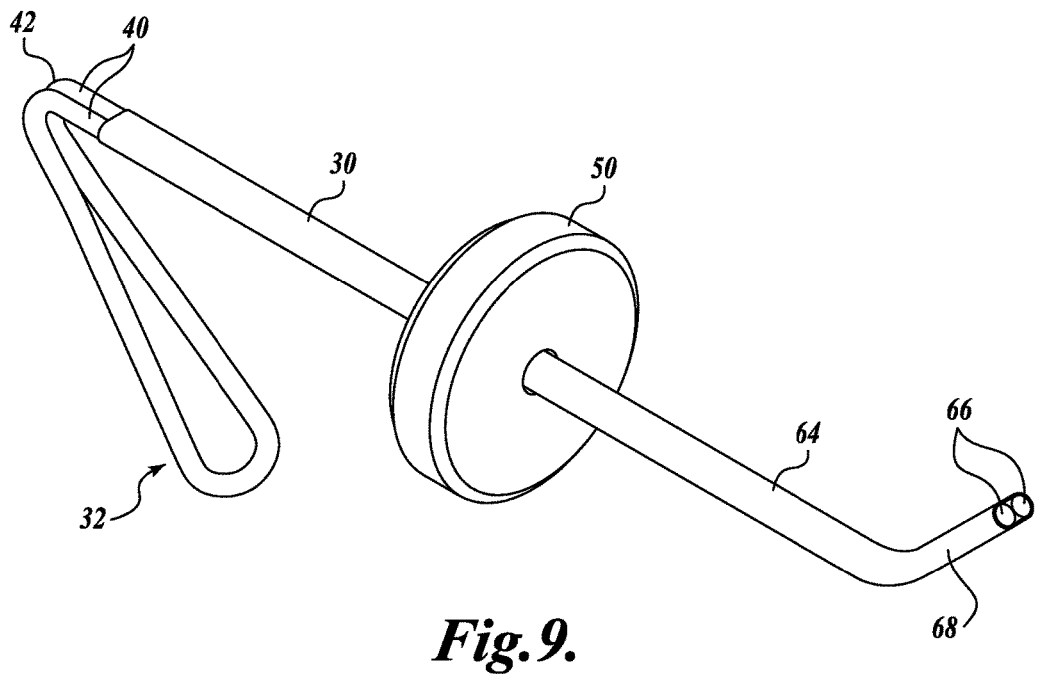
FIG. 9 is a top perspective of still another modified form of an instrument in accordance with the present invention, looking in a distal direction.

In the embodiment of FIG. 9, similar to the previously described embodiments, the instrument includes a shaft/handle portion 30 much longer than the resilient loop portion 32. The resilient loop portion 32 has the same shape and characteristics as the corresponding part of the embodiment of FIGS. 2A-2I. However, rather than using a separate rigid stainless steel cannula, the side-by-side portions 40 of the surgical plastic suture material are extended proximally from the reflex bend 42 and are held together by a longer length 64 of surgical grade, heat-shrinkable tubing or film, preferably polyester. The extended proximate sections of suture form the core of the intermediate shank. The tubing encases and stiffens the long intermediate stretches of suture or strand which extend all the way to the proximate ends 66 seen toward the right of FIG. 9. A resilient stopper 50 has a central aperture that fits snugly on the shaft portion 30 such that it can be adjusted along the length of the shaft portion. Similar to the stopper 50 for the previously described embodiment, the frictional engagement of the stopper on the shaft is loose enough for easy adjustment but snug enough for reliable positioning of the instrument during surgery. The proximate portion 68 of the instrument is angled slightly for ease in grasping and manipulation of the instrument, which typically will be by use of small forceps.

Figure 10:
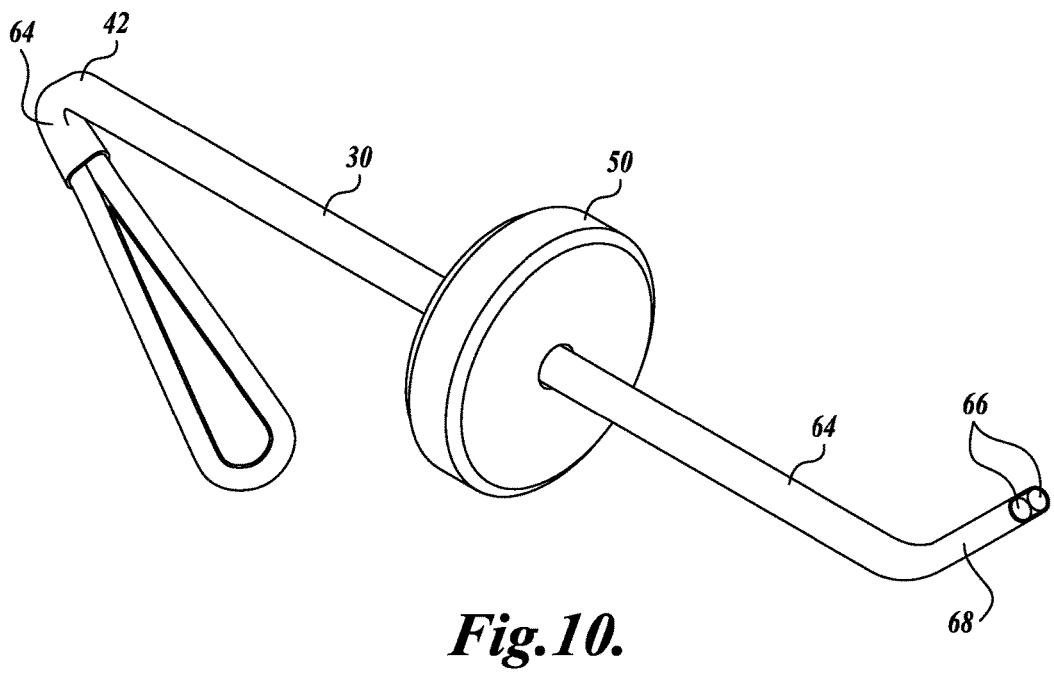
FIG. 10 is a corresponding perspective of an instrument similar to the instrument of FIG. 9 but with an additional modification at the distal end portion thereof.

The embodiment of FIG. 10 is identical to the embodiment of FIG. 9 except that the tubing 64 extends a short distance around the reflex bend 42 in the distal portion of the instrument.

Figure 11:
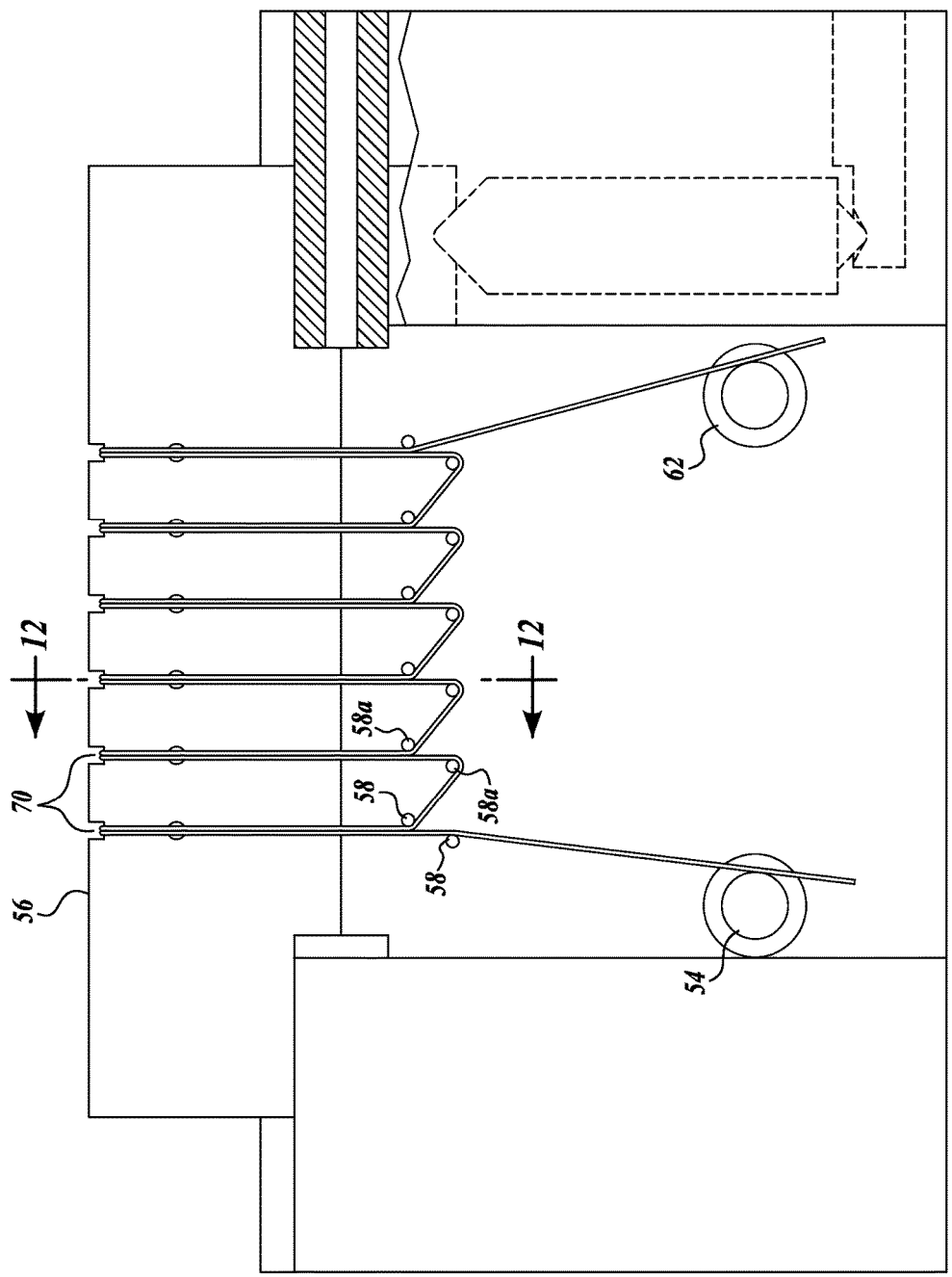
FIG. 11 is a diagrammatic top plan of a tool used during manufacture of the FIG. 9 embodiment of the present invention.
Figure 12:
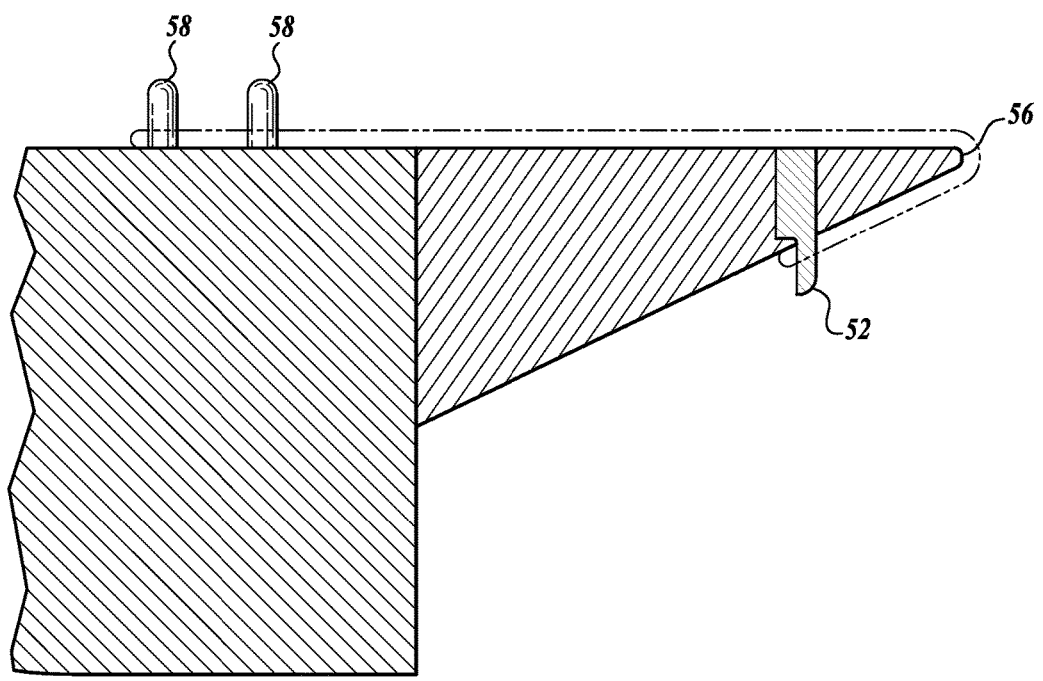
FIG. 12 is a diagrammatic, enlarged fragmentary section along line 12-12 of FIG. 11.

To form the embodiment of FIG. 9 or FIG. 10, first the suture material is positioned and heat treated to achieve the desired shape, then the surgical heat-shrinkable tubing is applied, and then the instrument is treated again to shrink the tubing. In the first stage of manufacture, illustrated in FIGS. 11-13, the suture material is tensioned on a positioning tool or jig, similar to the embodiments previously described. For example, FIG. 11 shows the top side of the jig. One end of a length of the suture material is clamped to the top side by a screw 54. The suture is tensioned and fitted between a first pair of rearwardly projecting pegs 58. From the pegs, the suture is wrapped around the tip 56 of a wedge section of the tool which has shallow rounded notches 70. As represented in the diagrammatic sectional view of FIG. 12, the suture is wound around a bottom peg 52 which is not necessarily circular in cross-section but which can be shaped to achieve a desired curvature for the resilient loop of the resulting instrument. From there, the suture is wrapped back through the same notch 70, between the pegs 58 (which are positioned to maintain the stretches along the top side essentially contiguously engaged), then to the next set of pegs 58a, continuing as for the previously described embodiment, until the final stretch is reached and the suture is clamped by a screw 62.

Figure 13:
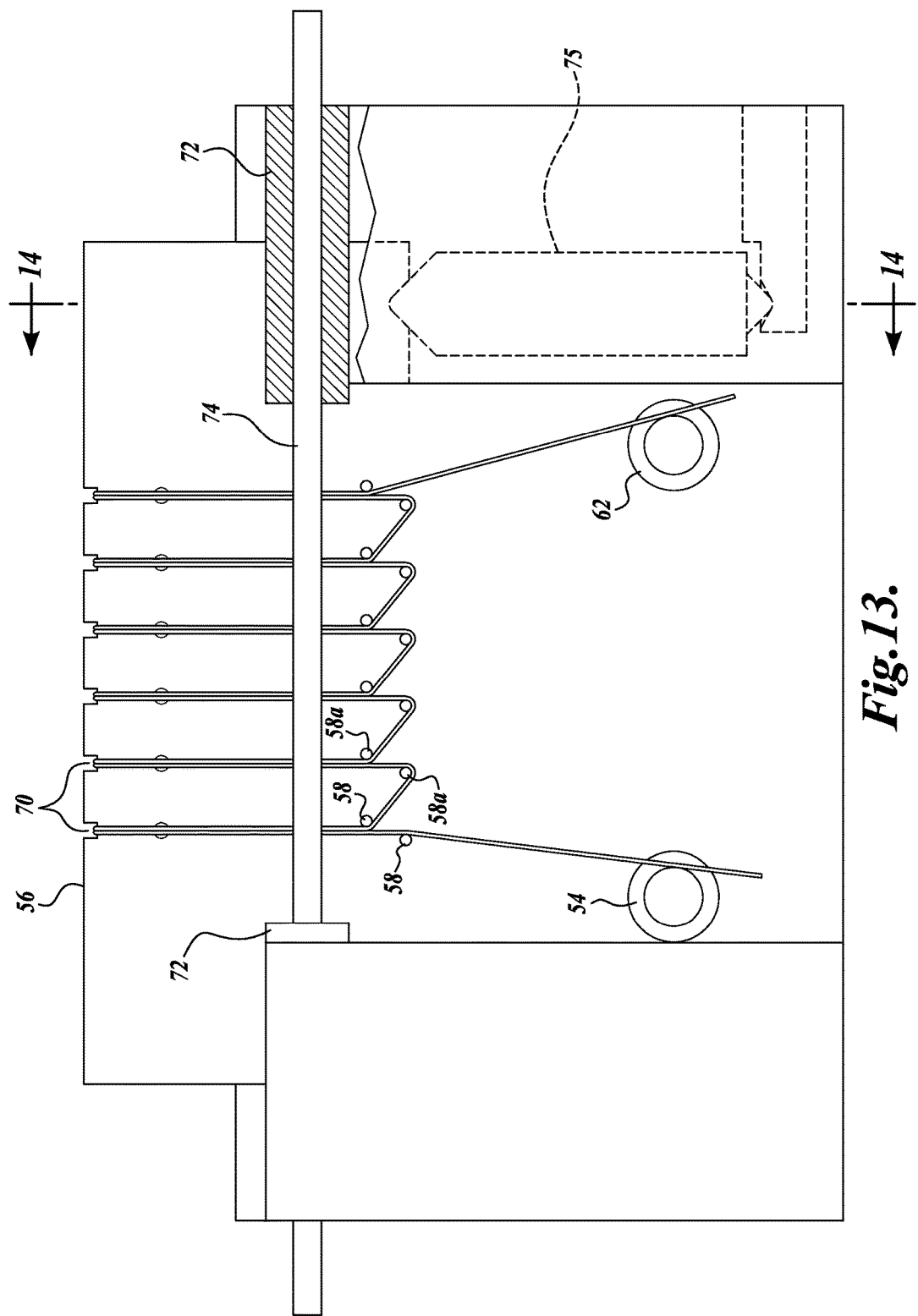
FIG. 13 is a top plan corresponding to FIG. 11, with an additional part inserted.
Figure 14A:
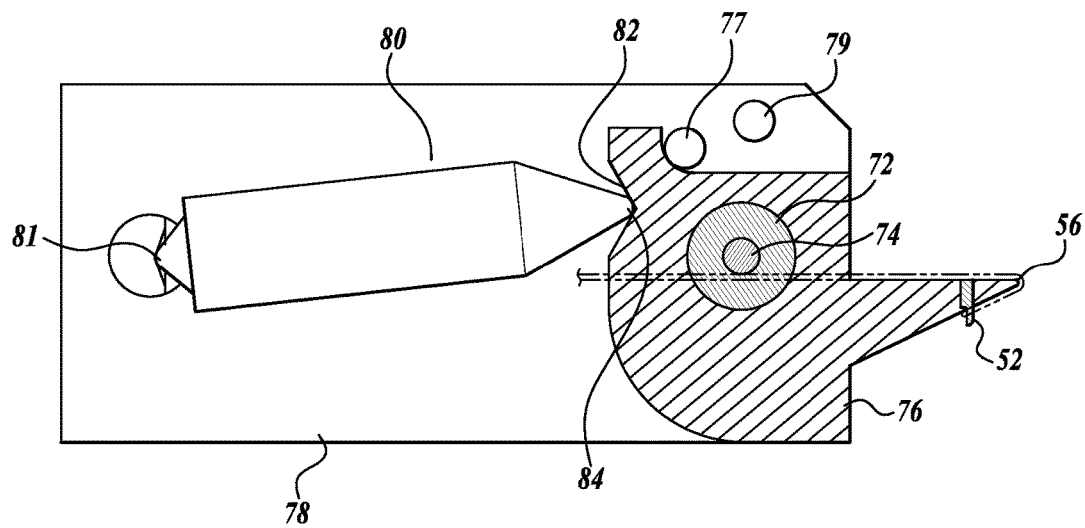
FIG. 14A is a diagrammatic side elevation of the tool with parts shown in section generally along line 14-14 of FIG. 13.
Figure 14B:
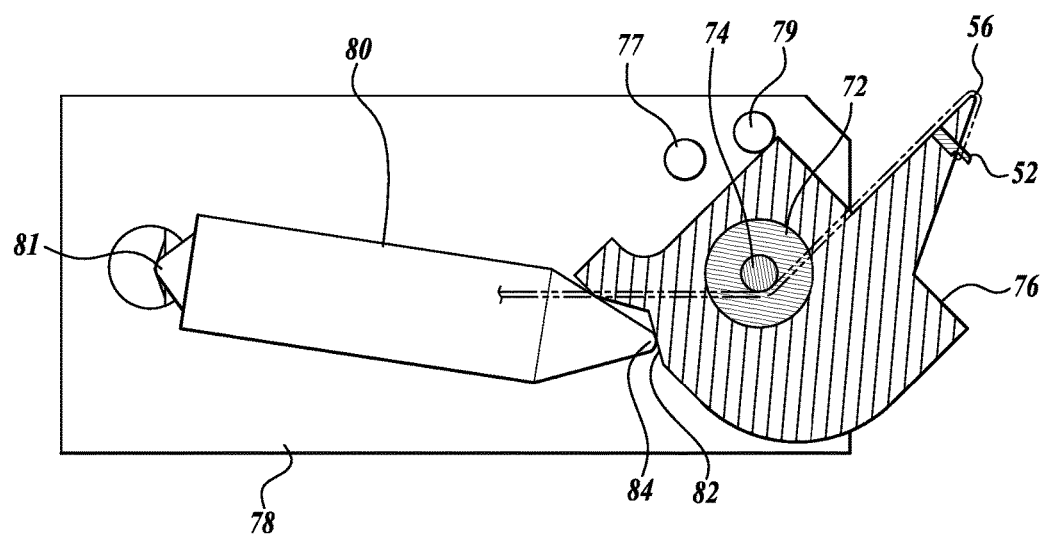
FIG. 14B is a side elevation and section corresponding to FIG. 14A but with parts in different positions.

At this point, prior to heat treating, the long, top side, intermediate stretches of the suture preferably are bent or angled to achieve the desired shape at the proximate, handle end portion. For this reason, the jig shown diagrammatically in FIGS. 11-14 has two parts that pivot relative to each other and which cooperate to hold the tensioned suture in the desired position. With reference to FIG. 13, the jig has coaxial bushings 72 which define the pivot axis for the separate parts. In addition, such bushings have coaxial bores for a rod 74 that is inserted to lie on top of the stretched suture at the location where the angled handle bend is desired. The jig has an over-center latch mechanism 75 which maintains the jig parts with their back faces coplanar for winding of the suture but which can be shifted, after positioning of the rod 74, to angle the proximate handle portions to the desired degree. The over-center mechanism is represented diagrammatically in FIG. 14A and FIG. 14B where some parts are shown in section. The jig has the front portion 76 that pivots relative to a rear portion 78. The over-center latch can include a spring-loaded plunger 80 having a base portion 81 pressing against the rear jig part 78 and a tip 82 that fits in a notch 84 of the front jig part 76 to maintain the desired relative positions of the jig parts, in cooperation with appropriate stops, such as pins or pegs 77, 79. FIG. 14A represents the relative positions for winding and tensioning the suture (shown in broken lines) to the configuration of FIG. 11. After winding and tensioning, and installation of the rod 74, the front part is swung to the position of FIG. 14B. The geometry is such that the over-center plunger 80 maintains the jig parts 76, 78 in the angled position because the force of the plunger is now applied horizontally along a line of force below the pivot axis. With the wound suture thus held, heat treating can be as previously described. When the suture is cooled, it may be cut adjacent to the pegs 58 (FIG. 11 or 13), followed by application of the shrink tubing and heat treating of the shrink tubing to stiffen the shaft of the instrument as compared to the inherent resiliency of the suture strand.

The next step of manufacture is insertion of a desired stopper to be used in positioning the instrument during surgery. This can be achieved by inserting a hypodermic needle through the center of the stopper. The needle has a bore sized to receive the shank portion of the instrument. The stopper then is slid off the hypodermic needle as the needle is retracted, until the stopper is supported on the shank of the instrument with the desired frictional engagement.

Figure 15:
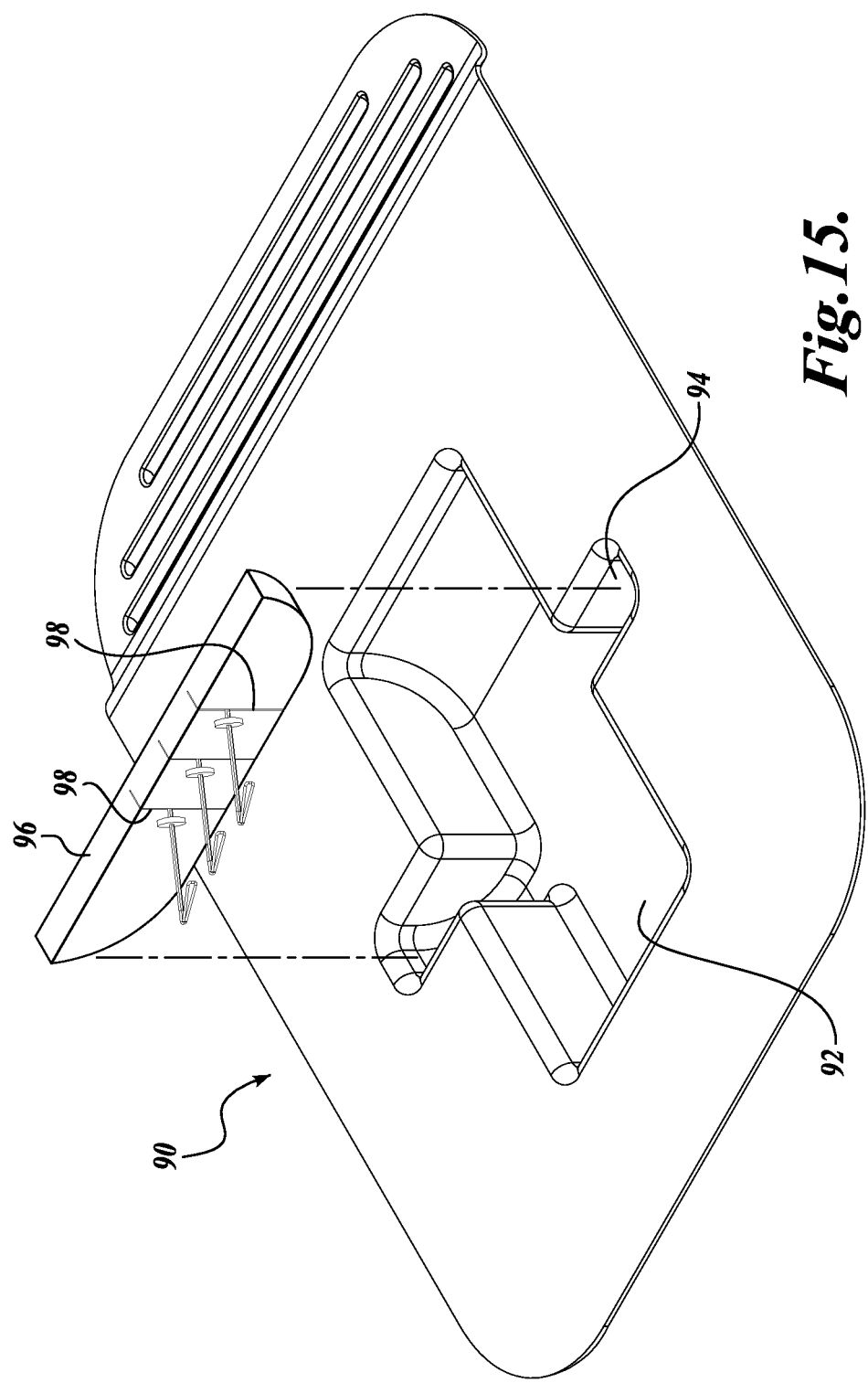
FIG. 15 is a diagrammatic top perspective of a set of instruments in accordance with the present invention and a package therefor, with some parts shown in an exploded relationship.
Figure 16:
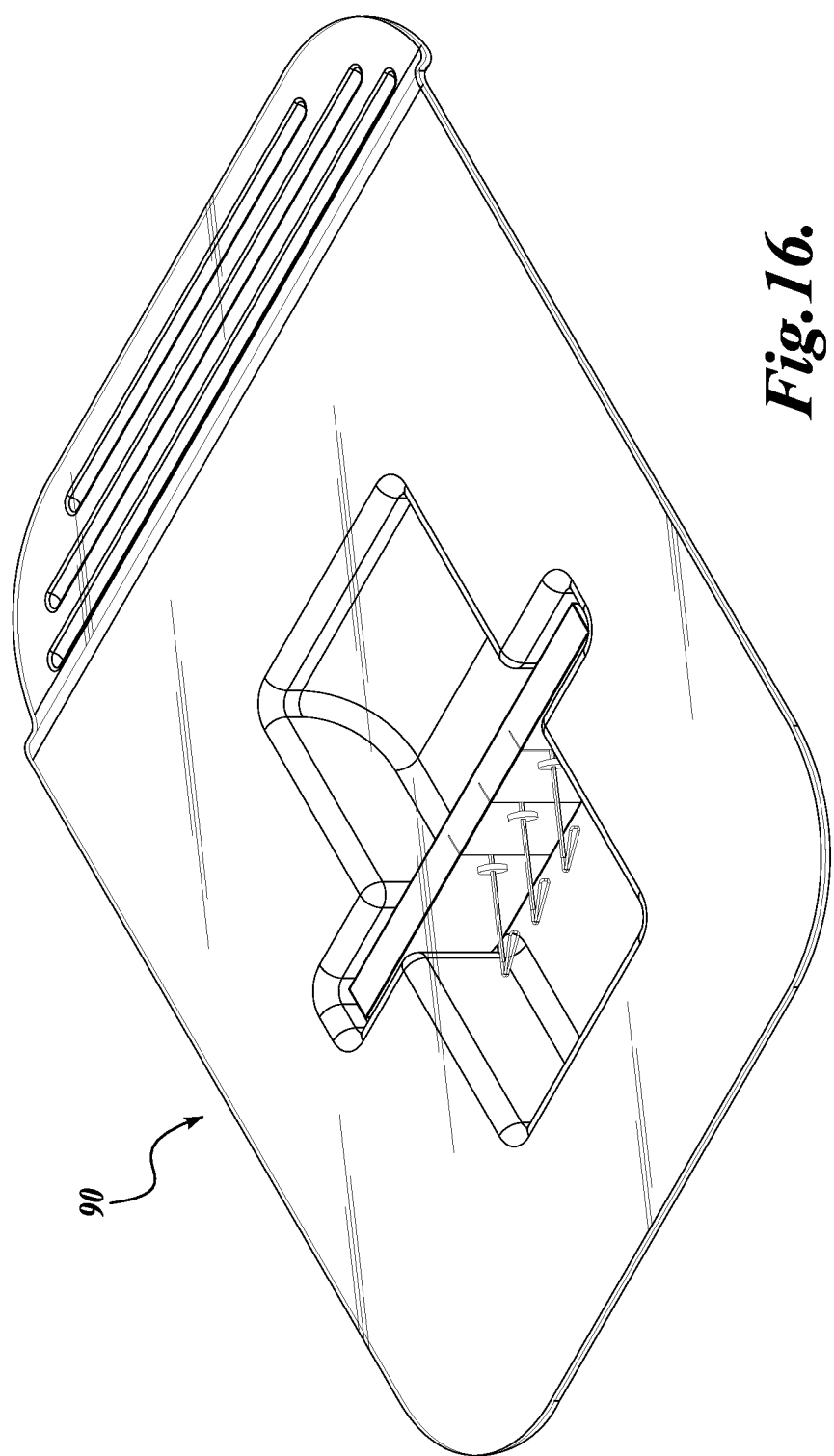
FIG. 16 is a top perspective corresponding to FIG. 15, but with parts assembled.
Figure 17:
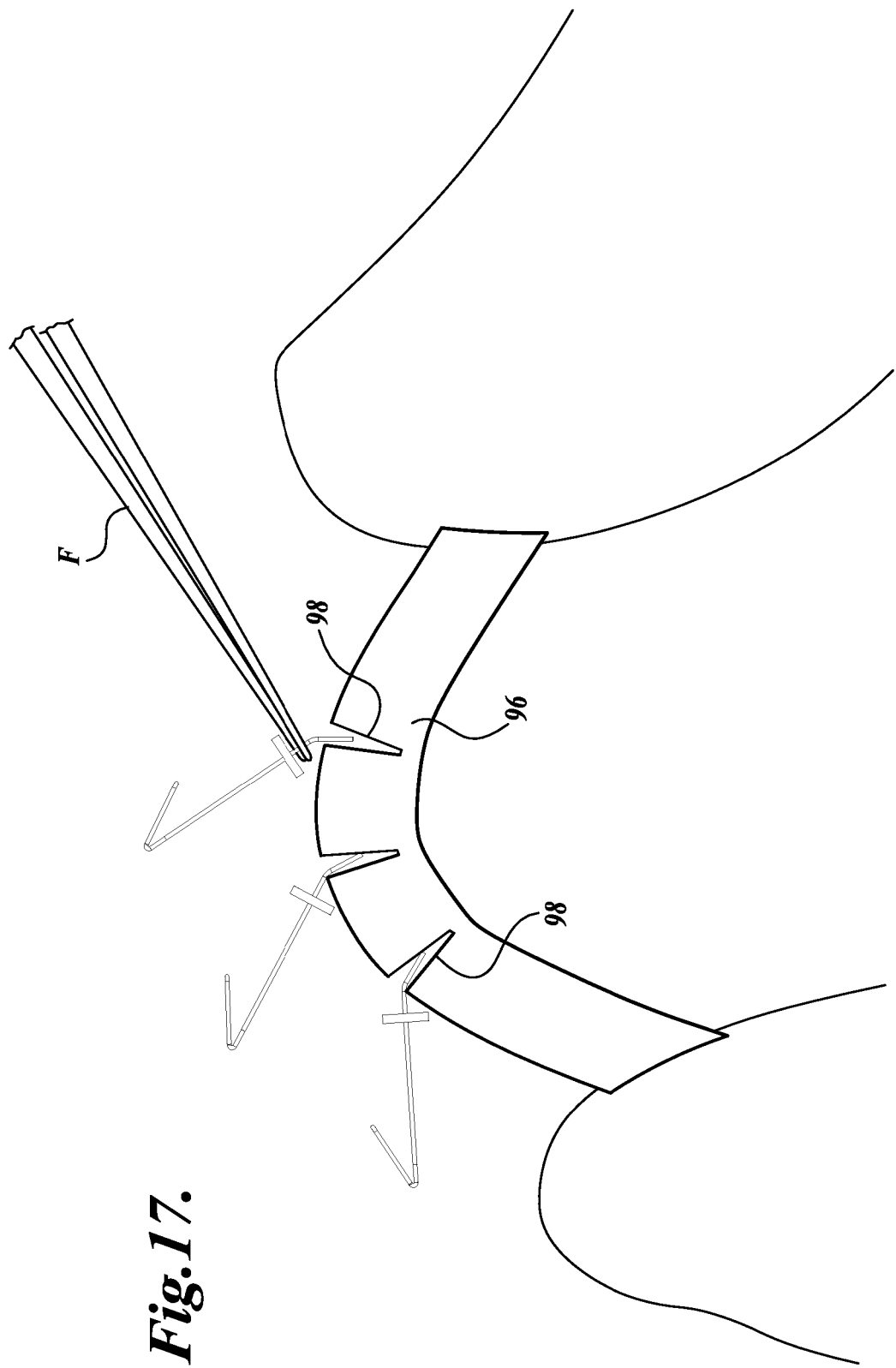
FIG. 17 is an enlarged diagrammatic top plan of a component of the package of FIG. 15 illustrating insertion of instruments in accordance with the present invention into a holder or removal of instruments from the holder.

With reference to FIGS. 15-17, sets of the instruments then can be packaged in a preformed plastic container 90. The base of the container has a cavity 92 with notches 94 in opposite sides that form upward opening grooves to receive opposite end portions of a transverse mounting bar 96. The bar is formed of resilient material such as a silicone plastic. One upright face of the bar has a series of vertical slits 98. The instruments to be packaged can have their proximate end portions fitted in the slits such that they are resiliently grasped and maintained in a centered, horizontally projecting position. When the bar is fitted in the base of the container, the instruments are cantilevered from the bar without engaging other surrounding structure, as seen in FIG. 16. In the condition of FIG. 16, the cavity, mounting bar, and instruments have been sealed by a lid. FIG. 17 illustrates the procedure for inserting the proximate end portions of the instruments into the bar, which can be achieved by bending the bar to spread apart the slits. The instruments can be manipulated by suitable forceps F, which is the same technique used for removing the instruments at the time of use. The packaging operation will be conducted in a clean room to assure sterile conditions. In FIGS. 15-17, a set of three instruments is shown, but fewer or more could be included in a package.

Figure 18:
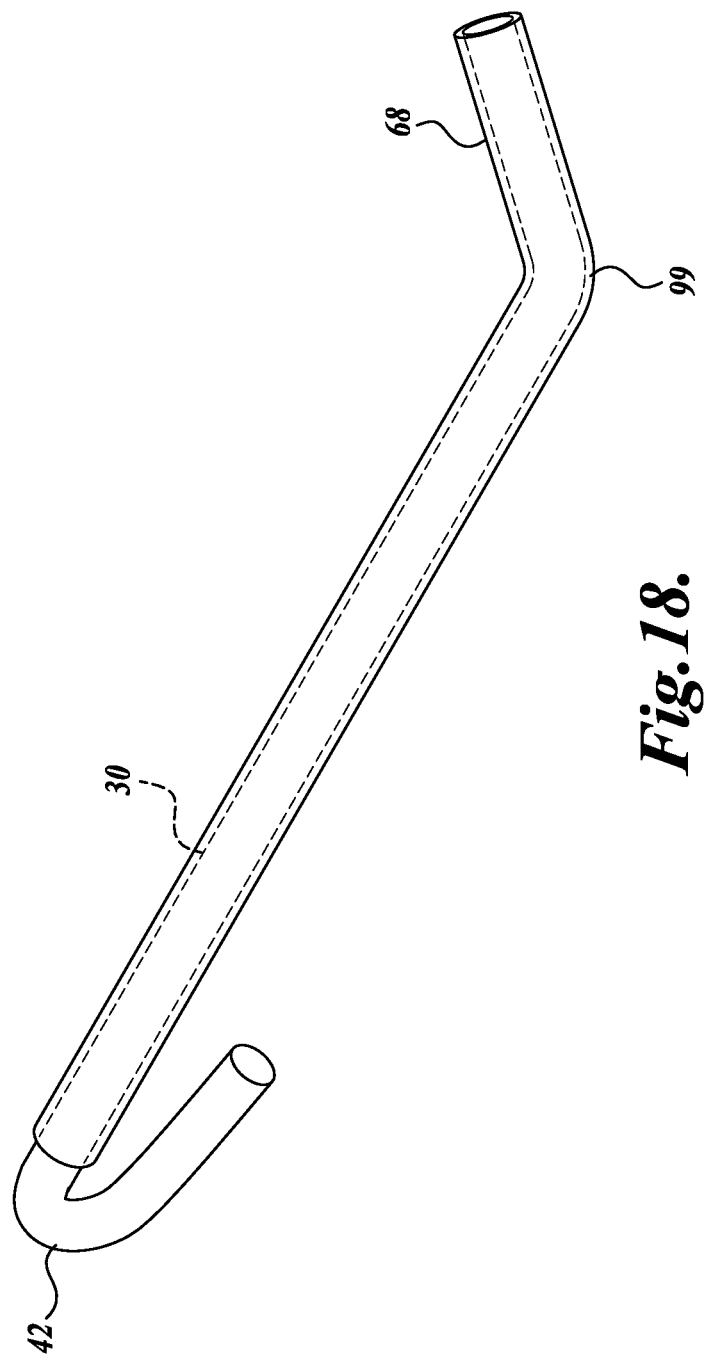
FIG. 18 is a top perspective of an additional embodiment of an instrument in accordance with the present invention viewed from the top and toward the distal end portion thereof.

The embodiments thus far described have looped or arcuate free end portions for engaging the interior of a lens capsule. The instrument of FIG. 18 uses a single, unitary strand or filament of resilient material such as surgical plastic suture of the type described above. The strand is formed with an elongated intermediate shank portion 30 having a reflex bend 42 in the distal end portion and an obtuse bend 99 toward the proximate end portion 68. The distal end portion of the instrument forms a hook to engage, for example, the iris and/or a portion of the capsular bag. The angled proximate end portion makes it easier to grasp and manipulate the hook. At least the major portion of the intermediate shank 30 is encased in a layer of material to stiffen the shank, as compared to the hook which has only the inherent resiliency of the strand material. Preferably, the stiffening layer is heat-shrinkable material, preferably thin surgical grade heat-shrinkable tubing 64 which rigidifies the intermediate shank sufficiently that it can be reliably manipulated by the surgeon or an attendant during intracapsular ophthalmic surgery where the instrument can be used for retracting or holding the iris and/or a portion of the capsular bag, or to hook or position other components or materials used during surgery, such as by hooking a capsular tension ring (CTR) or a CTR segment or an eyelet of a CTR ring or segment. Depending on the use, a stopper can be positioned on the shank.

While the preferred embodiment of the invention has been illustrated and described, it will be appreciated that various changes can be made therein without departing from the spirit and scope of the invention. For example, in the embodiments of FIGS. 2-8, stainless steel cannula and nylon suture are the currently preferred materials, but other materials can be used and other manners of securing the resilient member to the rigid shaft are possible, including epoxy or another adhesive. If an adhesive is used, the resilient member may need to be shaped with grooves or serrations to increase the adherence and lessen the prospects of the resilient member working loose.

The invention claimed is:

1. An instrument for use in ophthalmic surgery, said instrument comprising:
   a shank having an elongated intermediate portion;
   a proximate end portion joined to one end of the shank intermediate portion; and
   a distal end portion fixedly connected to and projecting from the end of the shank intermediate portion opposite the end to which the proximate end portion is joined, the distal end portion having a reflex bend formed by bending the distal end in a first plane such that the distal end portion is in the shape of a hook extending first in a distal direction and then in a proximate direction;
   wherein the distal end portion comprises a resilient strand, wherein at least the shank elongated intermediate portion has a stiffness greater than an inherent resiliency of the resilient strand, for positioning of the resilient strand during surgery by manipulation of the shank intermediate portion;
   wherein a free end of the resilient strand is a blunt, closed, arcuate loop having a fixed length with respect to the shank intermediate portion and formed by bending the resilient strand in a second plane perpendicular to the first plane, the free end of the resilient strand configured to engage an inner periphery of a capsular bag between the free end and the shank intermediate portion to stabilize the capsular bag during ophthalmic surgery, wherein a proximal end of the blunt, closed, arcuate loop is formed distal of the reflex bend; and
   wherein the resilient strand comprises adjacent stretches that form the distal end portion including the reflex bend.

2. The instrument defined in claim 1, in which the resilient strand is surgical suture material.

3. The instrument defined in claim 1, including a stopper frictionally engaged on the shank intermediate portion but adjustable therealong.

4. The instrument defined in claim 1, in which the arcuate free end portion of the loop has a flattened exterior.

5. The instrument defined in claim 1, in which the adjacent stretches include proximate sections extending along the length of and forming a core of the shank intermediate portion, the shank intermediate portion further including a layer of stiffening material encasing the proximate portions of the stretches.

6. The instrument defined in claim 5, in which the stiffening material is heat-shrinkable material secured on the proximate sections of the stretches by heat shrinking.

7. The instrument defined in claim 5, in which the proximate end portion is connected to the shank elongated intermediate portion by an obtuse bend.

8. The instrument defined in claim 7, in which the stiffening material and the proximate sections of the stretches extend along and form the proximate end portion.

9. The instrument defined in claim 5, in which the stiffening material encases the sections of the stretches that form the reflex bend.

10. The instrument defined in claim 1, in which the shank intermediate portion is a rigid cannula.

11. The instrument defined in claim 10, in which the resilient strand forms the distal end portion including the reflex bend.

12. The instrument defined in claim 1, in which the resilient strand has a free end formed as an eyelet with the adjacent stretches extending therefrom in a proximate direction and contiguously engaged.

13. The instrument defined in claim 12, in which the contiguously engaged stretches are encased in a layer of stiffening material.

14. The instrument defined in claim 1, in which the proximate end portion is connected to the shank elongated intermediate portion by an obtuse bend.

15. The instrument defined in claim 1, including a mounting bar of resilient material, the bar having a narrow slit in an upright side thereof, the proximate end portion being held in the slit and the shank intermediate portion being cantilevered from the bar.

16. The instrument defined in claim 15, including a container having a cavity, the bar being mounted in the container cavity with the shank intermediate portion, the distal portion, and the resilient strand projecting therefrom into the cavity without contacting any surrounding structure other than the bar.

17. An instrument for use in ophthalmic surgery, said instrument comprising:
    a shank having an elongated intermediate portion forming a handle; and
    a distal end portion fixedly connected to and projecting from the shank intermediate portion, the distal end portion having a reflex bend formed by bending the distal end in a first plane such that the distal end portion is in the shape of a hook extending first in a distal direction and then in a proximate direction;
    wherein the distal portion comprises a resilient strand and wherein the shank elongated intermediate portion has a stiffness greater than the inherent resiliency of the resilient strand, for positioning of the resilient strand during surgery by manipulation of the shank intermediate portion, the resilient strand having a blunt, closed, arcuate free end portion formed by bending the strand in a second plane perpendicular to the first plane to form a proximal end of the blunt, closed, arcuate free end portion at a point on the strand distal to the reflex bend and constructed and arranged to engage an inner periphery of a capsular bag between the free end and the shank intermediate portion to stabilize the capsular bag during ophthalmic surgery with the reflex bend extending from the interior of the bag to the anterior of the bag, the resilient strand having adjacent stretches extending alongside each other in a distal direction from the arcuate free end portion and forming the distal end portion including the reflex bend, the adjacent stretches having a fixed length with respect to the shank intermediate portion and including proximate sections extending along the length of and forming a core of the shank intermediate portion, the shank intermediate portion further including a layer of stiffening material encasing the proximate portions of the stretches.

18. The instrument defined in claim 17, in which the resilient strand is surgical suture material.

19. The instrument defined in claim 17, in which the stiffening material is heat-shrinkable material secured on the proximate sections of the stretches by heat shrinking.

* * * * *